(12) United States Patent
Sahin et al.

(10) Patent No.: US 9,979,451 B2
(45) Date of Patent: May 22, 2018

(54) METHOD AND APPARATUS FOR MULTILAYER TRANSMISSION AND HYBRID RELAYING WITH MULTIPLE OUT-OF-BAND RELAYS

(71) Applicants: INTERDIGITAL PATENT HOLDINGS, INC., Wilmington (DE); NEW JERSEY INSTITUTE OF TECHNOLOGY, Newark, NJ (US)

(72) Inventors: Onur Sahin, London (GB); Seok-Hwan Park, Millburn, NJ (US); Osvaldo Simeone, New York City, NY (US); Ariela Zeira, Huntington, NY (US)

(73) Assignees: INTERDIGITAL PATENT HOLDINGS, INC., Wilmington, DE (US); NEW JERSEY INSTITUTE OF TECHNOLOGY, Newark, NJ (US)

( * ) Notice: Subject to any disclaimer, the term of this patent is extended or adjusted under 35 U.S.C. 154(b) by 0 days. days.

(21) Appl. No.: 14/783,697

(22) PCT Filed: Apr. 11, 2014

(86) PCT No.: PCT/US2014/033729
§ 371 (c)(1),
(2) Date: Oct. 9, 2015

(87) PCT Pub. No.: WO2014/169169
PCT Pub. Date: Oct. 16, 2014

(65) Prior Publication Data
US 2016/0080055 A1 Mar. 17, 2016

Related U.S. Application Data

(60) Provisional application No. 61/811,404, filed on Apr. 12, 2013.

(51) Int. Cl.
*H04B 7/02* (2018.01)
*H04L 1/02* (2006.01)
(Continued)

(52) U.S. Cl.
CPC ......... *H04B 7/0473* (2013.01); *C07D 307/12* (2013.01); *C07D 307/24* (2013.01);
(Continued)

(58) Field of Classification Search
None
See application file for complete search history.

(56) References Cited

U.S. PATENT DOCUMENTS 8,225,168 B2 * 7/2012 Yu .................. H03M 13/114
370/216
8,873,621 B2 * 10/2014 Kim .................. 375/240.03
(Continued)

OTHER PUBLICATIONS

Cover et al., "Elements of Information Theory", Wiley Series in Telecomm., 1st ed., (1991).
(Continued)

*Primary Examiner* — Shuwang Liu
*Assistant Examiner* — Gina McKie
(74) *Attorney, Agent, or Firm* — Invention Mine LLC

(57) ABSTRACT

A method and apparatus for hybrid multi-layer transmission includes receiving a multi-layer signal from a source device, wherein the multi-layer signal includes a plurality of sublayers. A quantity of the plurality of sublayers is decoded and partial information relating to the decoded sublayers is transmitted to a destination device.

8 Claims, 7 Drawing Sheets

(51) Int. Cl.
| | |
|---|---|
| H04B 7/04 | (2017.01) |
| C07D 307/12 | (2006.01) |
| C07D 307/24 | (2006.01) |
| C08K 5/11 | (2006.01) |
| C08K 5/1535 | (2006.01) |
| C08K 5/42 | (2006.01) |
| H04B 7/155 | (2006.01) |
| H04W 88/08 | (2009.01) |

(52) U.S. Cl.
CPC .............. *C08K 5/11* (2013.01); *C08K 5/1535* (2013.01); *C08K 5/42* (2013.01); *H04B 7/155* (2013.01); *H04W 88/08* (2013.01)

(56) References Cited

U.S. PATENT DOCUMENTS

| | | | | |
|---|---|---|---|---|
| 2003/0202579 | A1* | 10/2003 | Lin | H04N 19/61 375/240.03 |
| 2008/0008247 | A1* | 1/2008 | Segall | H04N 19/70 375/240.18 |
| 2009/0175214 | A1* | 7/2009 | Sfar | H04B 7/15592 370/315 |
| 2011/0103296 | A1 | 5/2011 | Ji et al. | |
| 2011/0314303 | A1* | 12/2011 | Shevchenko | G06F 9/30178 713/190 |
| 2013/0010682 | A1 | 1/2013 | Kim et al. | |

OTHER PUBLICATIONS

Gamal et al., "Network Information Theory," Cambridge University Press, (2011).
Boyd et al., "Convex Optimization", Cambridge University Press, (2004).
Chechik et al., "Information Bottleneck for Gaussian Variables," Jour. Machine Learn., Res. 6, pp. 165-188, (2005).
Chen, "Capacity Theorems for Three-User Cooperative Relay Broadcast Channels", 2012 46$^{th}$ Annual Conference on Information Sciences and Systems (CISS), Princeton, NJ, pp. 1-6 (Mar. 21, 2012).
Cover, "Comments on Broadcast Channels," IEEE Trans. Inf. Theory, vol. 44, No. 6, pp. 2524-2530, (Oct. 1998).
De Bruyn et al., "Reliable Transmission of Two Correlated Sources over an Asymmetric Multiple-Access Channel," IEEE Trans. Inf. Theory, vol. 33, No. 5, pp. 716-718, (Sep. 1987).
Del Coso et al., "Achievable Rates for the AWGN Channel with Multiple Parallel Relays," IEEE Trans. Wireless Comm., vol. 8, No. 5, pp. 2524-2534, (May 2009).
Del Coso et al., "Distributed Compression for MIMO Coordinated Networks with a Backhaul Constraint," IEEE Trans. Wireless Comm., vol. 8, No. 9, pp. 4698-4709, (Sep. 2009).
Gunduz et al., "On the Capacity Region of a Multiple Access Channel with Common Messages," in Proc. IEEE Intern. Sym. Inf. Theory (ISIT 2010), Austin, TX, pp. 470-474, (Jun. 2010).

Marsch et al., "Future Mobile Communication Networks: Challenges in the Design and Operation," IEEE Veh. Tech. Mag., vol. 7, No. 1, pp. 16-23, (Mar. 2012).
Nazer et al., "Structured Superposition for Backhaul Constrained Cellular Uplink," in Proc. IEEE Intern. Sym. Inf. Theory (ISIT 2009), Seoul, Korea, pp. 1530-1534, (Jun. 2009).
Park et al., "Robust and Efficient Distributed Compression for Cloud Radio Access Networks," IEEE Transactions on Vehicular Technology, vol. 62, No. 2, pp. 692-703, (Feb. 2013).
Sanderovich et al., "Communication Via Decentralized Processing," IEEE Trans. Inf. Theory, vol. 54, No. 7, pp. 3008-3023, (Jul. 2008).
Sanderovich et al., "Uplink Macro Diversity of Limited Backhaul Cellular Network," IEEE Trans. Inf. Theory, vol. 55, No. 8, pp. 3457-3478, (Aug. 2009).
Segel et al., "Lightradio portfolio-technical overview," Technology White Paper 1, Alcatel-Lucent, (2011).
Schein, "Distributed Coordination in Network Information Theory," Ph.D., MIT, Cambridge, MA, (2001).
Shamai et al., "A Broadcast Approach for a Single-User Slowly Fading MIMO Channel," IEEE Trans. Inf. Theory, vol. 49, No. 10, pp. 2617-2635, (Oct. 2003).
Simeone et al., "Cooperative Wireless Cellular Systems: An Information-Theoretic View," Foundations and Trends in Comm. Inf. Theory, vol. 8, No. 1-2, pp. 1-177 (2012).
Tian et al., "Remote Vector Gaussian Source Coding With Decoder Side Information Under Mutual Information and Distortion Constraints," IEEE Trans. Inf. Theory, vol. 55, No. 10, pp. 4676-4680, (Oct. 2009).
Wang et al., "Nested Cooperative Encoding Protocol for Wireless Networks with High Energy Efficiency", IEEE Transactions on Wireless Communications, vol. 7, No. 2, pp. 521-531 (Feb. 1, 2008).
Weeraddana et al., "Weighted Sum-Rate Maximization in Wireless Networks: A Review," Foundations and Trends in Networking, vol. 6, No. 1-2, pp. 1-163, (2012).
Wyner et al., "The Rate-Distortion Function for Source Coding with Side Information at the Decoder," IEEE Trans. Inf. Theory, vol. 22, No. 1, pp. 1-10, (Jan. 1976).
Xue et al., "Cooperation in a Half-Duplex Gaussian Diamond Relay Channel," IEEE Trans. Inf. Theory, vol. 53, No. 10, pp. 3806-3814 (Oct. 2007).
Zamani et al., "On the Maximum Achievable Rates in the Decode-Forward Diamond Channel", 2011 IEEE International Symposium on Information Theory Proceedings (ISIT) pp. 1534-1538, (Jul. 31-Aug. 5, 2011).
Zamani et al., "Broadcast Approaches to the Diamond Channel," IEEE Transactions on Information Theory, vol. 60, No. 1, pp. 623-642, (Jan. 2014).
Zhang et al., "Successive Decoding in Multiuser Information Theory," IEEE Trans. Inf. Theory, vol. 53, No. 6, pp. 2246-2254, (Jun. 2007).
Zhou et al., "Uplink Multicell Processing with Limited Backhaul via Successive Interference Cancellation," in Proc. IEEE Glob. Comm. Conf. (Globecom 2012), pp. 2322-2327, (Dec. 2012).

\* cited by examiner

METHOD AND APPARATUS FOR MULTILAYER TRANSMISSION AND HYBRID RELAYING WITH MULTIPLE OUT-OF-BAND RELAYS

CROSS REFERENCE TO RELATED APPLICATIONS

This application claims the benefit of U.S. Provisional Patent Application No. 61/811,404 filed Apr. 12, 2013, the contents of which are hereby incorporated by reference herein.

BACKGROUND

Multiple relay networks, in which a source encoder communicates with a destination device through a number of relays, may be utilized for a wide range of applications. Activity in a multiple relay network may focus on Gaussian networks in which a first hop amounts to a Gaussian broadcast channel from a source device to relays, and a second hop to a multiple access channel between relays and receivers. Various transmission strategies, including decode-and-forward (DF), compress-and-forward (CF), amplify-and-forward (AF) and hybrid AF-DF, may be utilized for communication in such a network.

In a variation of a classical multi-relay channel, relays may be connected to the destination through digital backhaul links of finite-capacity. For example, this model may be utilized in cloud radio cellular networks, in which the base stations (BSs) may act as relays connected to the central decoder via finite-capacity backhaul links.

Pooling multiple relays into a distributed multiple-input multiple-output (MIMO) system includes a number of issues that may need to be addressed. High-performance operation of such systems may require a centralized data and channel processor, which may place significant throughput and latency requirements on the backhaul links which connect the relays to the centralized processor. For example, in cloud radio cellular networks, where base stations act as relays connected to the central decoder in the cloud, the backhaul problem may be acute because the links may have a finite capacity that may be insufficient for traditional approaches.

SUMMARY

A method and apparatus for hybrid multi-layer transmission is disclosed. The method includes receiving a multi-layer signal from a source device, wherein the multi-layer signal includes a plurality of sublayers. A quantity of the plurality of sublayers is decoded and partial information relating to the decoded sublayers is transmitted to a destination device.

BRIEF DESCRIPTION OF THE DRAWINGS

A more detailed understanding may be had from the following description, given by way of example in conjunction with the accompanying drawings wherein.

DETAILED DESCRIPTION

Figure 1A:
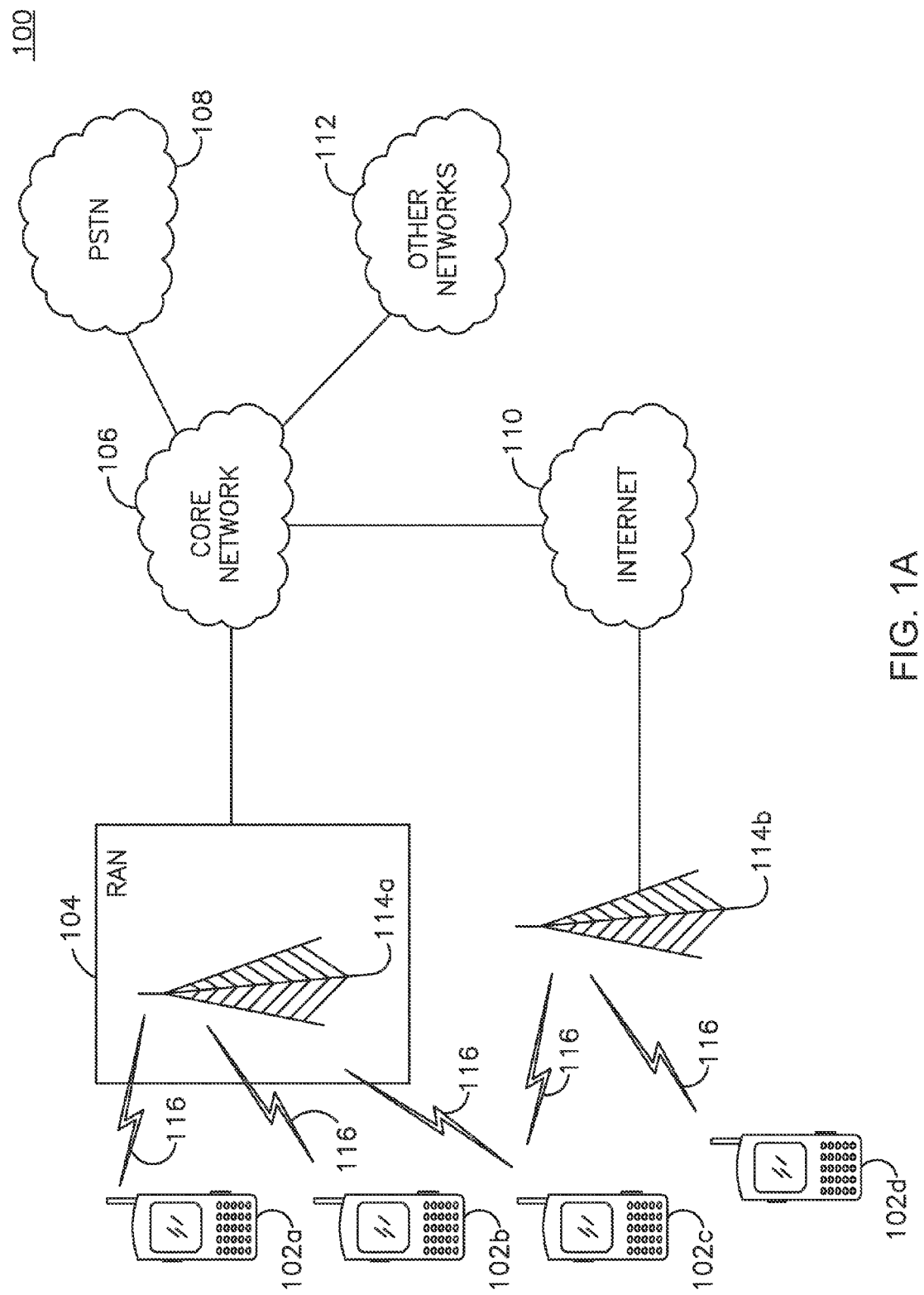
FIG. 1A is a system diagram of an example communications system in which one or more disclosed embodiments may be implemented.

FIG. 1A is a diagram of an example communications system 100 in which one or more disclosed embodiments may be implemented. The communications system 100 may be a multiple access system that provides content, such as voice, data, video, messaging, broadcast, etc., to multiple wireless users. The communications system 100 may enable multiple wireless users to access such content through the sharing of system resources, including wireless bandwidth. For example, the communications systems 100 may employ one or more channel access methods, such as code division multiple access (CDMA), time division multiple access (TDMA), frequency division multiple access (FDMA), orthogonal FDMA (OFDMA), single-carrier FDMA (SC-FDMA), and the like.

As shown in FIG. 1A, the communications system 100 may include wireless transmit/receive units (WTRUs) 102a, 102b, 102c, 102d, a radio access network (RAN) 104, a core network 106, a public switched telephone network (PSTN) 108, the Internet 110, and other networks 112, though it will be appreciated that the disclosed embodiments contemplate any number of WTRUs, base stations, networks, and/or network elements. Each of the WTRUs 102a, 102b, 102c, 102d may be any type of device configured to operate and/or communicate in a wireless environment. By way of example, the WTRUs 102a, 102b, 102c, 102d may be configured to transmit and/or receive wireless signals and may include user equipment (UE), a mobile station, a fixed or mobile subscriber unit, a pager, a cellular telephone, a personal digital assistant (PDA), a smartphone, a laptop, a netbook, a personal computer, a wireless sensor, consumer electronics, and the like.

The communications systems 100 may also include a base station 114a and a base station 114b. Each of the base stations 114a, 114b may be any type of device configured to wirelessly interface with at least one of the WTRUs 102a, 102b, 102c, 102d to facilitate access to one or more communication networks, such as the core network 106, the Internet 110, and/or the other networks 112. By way of example, the base stations 114a, 114b may be a base transceiver station (BTS), a Node-B, an eNode B, a Home Node B, a Home eNode B, a site controller, an access point (AP), a wireless router, and the like. While the base stations 114a, 114b are each depicted as a single element, it will be appreciated that the base stations 114a, 114b may include any number of interconnected base stations and/or network elements.

The base station 114a may be part of the RAN 104, which may also include other base stations and/or network elements (not shown), such as a base station controller (BSC), a radio network controller (RNC), relay nodes, etc. The base station 114a and/or the base station 114b may be configured to transmit and/or receive wireless signals within a particular geographic region, which may be referred to as a cell (not shown). The cell may further be divided into cell sectors. For example, the cell associated with the base station 114a may be divided into three sectors. Thus, in one embodiment, the base station 114a may include three transceivers, i.e., one for each sector of the cell. In another embodiment, the base station 114a may employ multiple-input multiple-output (MIMO) technology and, therefore, may utilize multiple transceivers for each sector of the cell.

The base stations 114a, 114b may communicate with one or more of the WTRUs 102a, 102b, 102c, 102d over an air interface 116, which may be any suitable wireless communication link (e.g., radio frequency (RF), microwave, infrared (IR), ultraviolet (UV), visible light, etc.). The air interface 116 may be established using any suitable radio access technology (RAT).

More specifically, as noted above, the communications system 100 may be a multiple access system and may employ one or more channel access schemes, such as CDMA, TDMA, FDMA, OFDMA, SC-FDMA, and the like. For example, the base station 114a in the RAN 104 and the WTRUs 102a, 102b, 102c may implement a radio technology such as Universal Mobile Telecommunications System (UMTS) Terrestrial Radio Access (UTRA), which may establish the air interface 116 using wideband CDMA (WCDMA). WCDMA may include communication protocols such as High-Speed Packet Access (HSPA) and/or Evolved HSPA (HSPA+). HSPA may include High-Speed Downlink Packet Access (HSDPA) and/or High-Speed Uplink Packet Access (HSUPA).

In another embodiment, the base station 114a and the WTRUs 102a, 102b, 102c may implement a radio technology such as Evolved UMTS Terrestrial Radio Access (E-UTRA), which may establish the air interface 116 using Long Term Evolution (LTE) and/or LTE-Advanced (LTE-A).

In other embodiments, the base station 114a and the WTRUs 102a, 102b, 102c may implement radio technologies such as IEEE 802.16 (i.e., Worldwide Interoperability for Microwave Access (WiMAX)), CDMA2000, CDMA2000 1x, CDMA2000 EV-DO, Interim Standard 2000 (IS-2000), Interim Standard 95 (IS-95), Interim Standard 856 (IS-856), Global System for Mobile communications (GSM), Enhanced Data rates for GSM Evolution (EDGE), GSM EDGE (GERAN), and the like.

The base station 114b in FIG. 1A may be a wireless router, Home Node B, Home eNode B, or access point, for example, and may utilize any suitable RAT for facilitating wireless connectivity in a localized area, such as a place of business, a home, a vehicle, a campus, and the like. In one embodiment, the base station 114b and the WTRUs 102c, 102d may implement a radio technology such as IEEE 802.11 to establish a wireless local area network (WLAN). In another embodiment, the base station 114b and the WTRUs 102c, 102d may implement a radio technology such as IEEE 802.15 to establish a wireless personal area network (WPAN). In yet another embodiment, the base station 114b and the WTRUs 102c, 102d may utilize a cellular-based RAT (e.g., WCDMA, CDMA2000, GSM, LTE, LTE-A, etc.) to establish a picocell or femtocell. As shown in FIG. 1A, the base station 114b may have a direct connection to the Internet 110. Thus, the base station 114b may not be required to access the Internet 110 via the core network 106.

The RAN 104 may be in communication with the core network 106, which may be any type of network configured to provide voice, data, applications, and/or voice over internet protocol (VoIP) services to one or more of the WTRUs 102a, 102b, 102c, 102d. For example, the core network 106 may provide call control, billing services, mobile location-based services, pre-paid calling, Internet connectivity, video distribution, etc., and/or perform high-level security functions, such as user authentication. Although not shown in FIG. 1A, it will be appreciated that the RAN 104 and/or the core network 106 may be in direct or indirect communication with other RANs that employ the same RAT as the RAN 104 or a different RAT. For example, in addition to being connected to the RAN 104, which may be utilizing an E-UTRA radio technology, the core network 106 may also be in communication with another RAN (not shown) employing a GSM radio technology.

The core network 106 may also serve as a gateway for the WTRUs 102a, 102b, 102c, 102d to access the PSTN 108, the Internet 110, and/or other networks 112. The PSTN 108 may include circuit-switched telephone networks that provide plain old telephone service (POTS). The Internet 110 may include a global system of interconnected computer networks and devices that use common communication protocols, such as the transmission control protocol (TCP), user datagram protocol (UDP) and the internet protocol (IP) in the TCP/IP internet protocol suite. The networks 112 may include wired or wireless communications networks owned and/or operated by other service providers. For example, the networks 112 may include another core network connected to one or more RANs, which may employ the same RAT as the RAN 104 or a different RAT.

Some or all of the WTRUs 102a, 102b, 102c, 102d in the communications system 100 may include multi-mode capabilities, i.e., the WTRUs 102a, 102b, 102c, 102d may include multiple transceivers for communicating with different wireless networks over different wireless links. For example, the WTRU 102c shown in FIG. 1A may be configured to communicate with the base station 114a, which may employ a cellular-based radio technology, and with the base station 114b, which may employ an IEEE 802 radio technology.

Figure 1B:
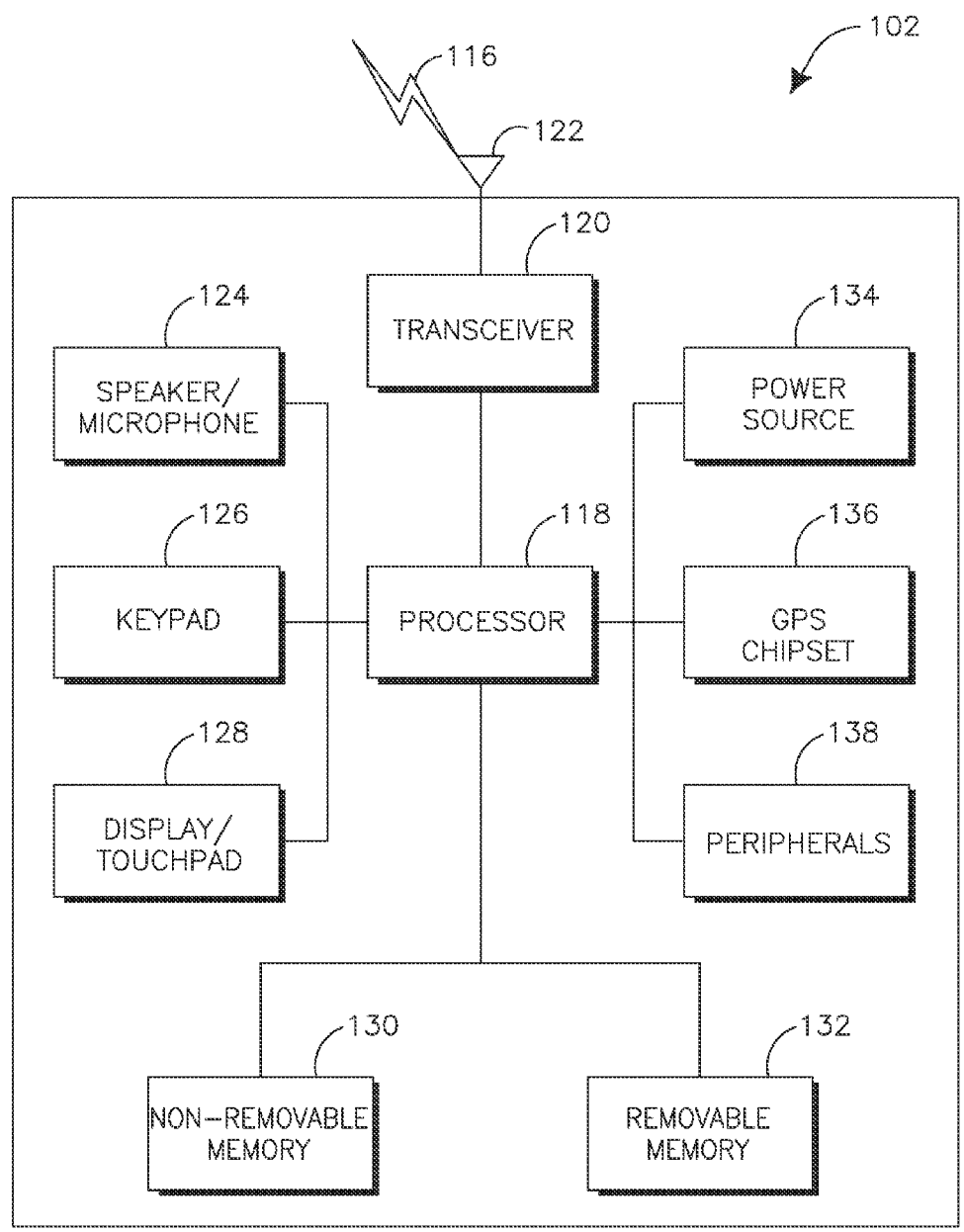
FIG. 1B is a system diagram of an example wireless transmit/receive unit (WTRU) that may be used within the communications system illustrated in FIG. 1A.

FIG. 1B is a system diagram of an example WTRU 102. As shown in FIG. 1B, the WTRU 102 may include a processor 118, a transceiver 120, a transmit/receive element 122, a speaker/microphone 124, a keypad 126, a display/touchpad 128, non-removable memory 130, removable memory 132, a power source 134, a global positioning system (GPS) chipset 136, and other peripherals 138. It will be appreciated that the WTRU 102 may include any sub-combination of the foregoing elements while remaining consistent with an embodiment.

The processor 118 may be a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Array (FPGAs) circuits, any other type of integrated circuit (IC), a state machine, and the like. The processor 118 may perform signal coding, data processing, power control, input/output processing, and/or any other functionality that enables the WTRU 102 to operate in a wireless environment. The processor 118 may be coupled to the transceiver 120, which may be coupled to the transmit/receive element 122. While FIG. 1B depicts the processor 118 and the transceiver 120 as separate components, it will be appreciated that the processor 118 and the transceiver 120 may be integrated together in an electronic package or chip.

The transmit/receive element 122 may be configured to transmit signals to, or receive signals from, a base station (e.g., the base station 114a) over the air interface 116. For example, in one embodiment, the transmit/receive element 122 may be an antenna configured to transmit and/or receive RF signals. In another embodiment, the transmit/receive element 122 may be an emitter/detector configured to transmit and/or receive IR, UV, or visible light signals, for example. In yet another embodiment, the transmit/receive element 122 may be configured to transmit and receive both RF and light signals. It will be appreciated that the transmit/receive element 122 may be configured to transmit and/or receive any combination of wireless signals.

In addition, although the transmit/receive element 122 is depicted in FIG. 1B as a single element, the WTRU 102 may include any number of transmit/receive elements 122. More specifically, the WTRU 102 may employ MIMO technology. Thus, in one embodiment, the WTRU 102 may include two or more transmit/receive elements 122 (e.g., multiple antennas) for transmitting and receiving wireless signals over the air interface 116.

The transceiver 120 may be configured to modulate the signals that are to be transmitted by the transmit/receive element 122 and to demodulate the signals that are received by the transmit/receive element 122. As noted above, the WTRU 102 may have multi-mode capabilities. Thus, the transceiver 120 may include multiple transceivers for enabling the WTRU 102 to communicate via multiple RATs, such as UTRA and IEEE 802.11, for example.

The processor 118 of the WTRU 102 may be coupled to, and may receive user input data from, the speaker/microphone 124, the keypad 126, and/or the display/touchpad 128 (e.g., a liquid crystal display (LCD) display unit or organic light-emitting diode (OLED) display unit). The processor 118 may also output user data to the speaker/microphone 124, the keypad 126, and/or the display/touchpad 128. In addition, the processor 118 may access information from, and store data in, any type of suitable memory, such as the non-removable memory 130 and/or the removable memory 132. The non-removable memory 130 may include random-access memory (RAM), read-only memory (ROM), a hard disk, or any other type of memory storage device. The removable memory 132 may include a subscriber identity module (SIM) card, a memory stick, a secure digital (SD) memory card, and the like. In other embodiments, the processor 118 may access information from, and store data in, memory that is not physically located on the WTRU 102, such as on a server or a home computer (not shown).

The processor 118 may receive power from the power source 134, and may be configured to distribute and/or control the power to the other components in the WTRU 102. The power source 134 may be any suitable device for powering the WTRU 102. For example, the power source 134 may include one or more dry cell batteries (e.g., nickel-cadmium (NiCd), nickel-zinc (NiZn), nickel metal hydride (NiMH), lithium-ion (Li-ion), etc.), solar cells, fuel cells, and the like.

The processor 118 may also be coupled to the GPS chipset 136, which may be configured to provide location information (e.g., longitude and latitude) regarding the current location of the WTRU 102. In addition to, or in lieu of, the information from the GPS chipset 136, the WTRU 102 may receive location information over the air interface 116 from a base station (e.g., base stations 114a, 114b) and/or determine its location based on the timing of the signals being received from two or more nearby base stations. It will be appreciated that the WTRU 102 may acquire location information by way of any suitable location-determination method while remaining consistent with an embodiment.

The processor 118 may further be coupled to other peripherals 138, which may include one or more software and/or hardware modules that provide additional features, functionality and/or wired or wireless connectivity. For example, the peripherals 138 may include an accelerometer, an e-compass, a satellite transceiver, a digital camera (for photographs or video), a universal serial bus (USB) port, a vibration device, a television transceiver, a hands free headset, a Bluetooth® module, a frequency modulated (FM) radio unit, a digital music player, a media player, a video game player module, an Internet browser, and the like.

Figure 1C:
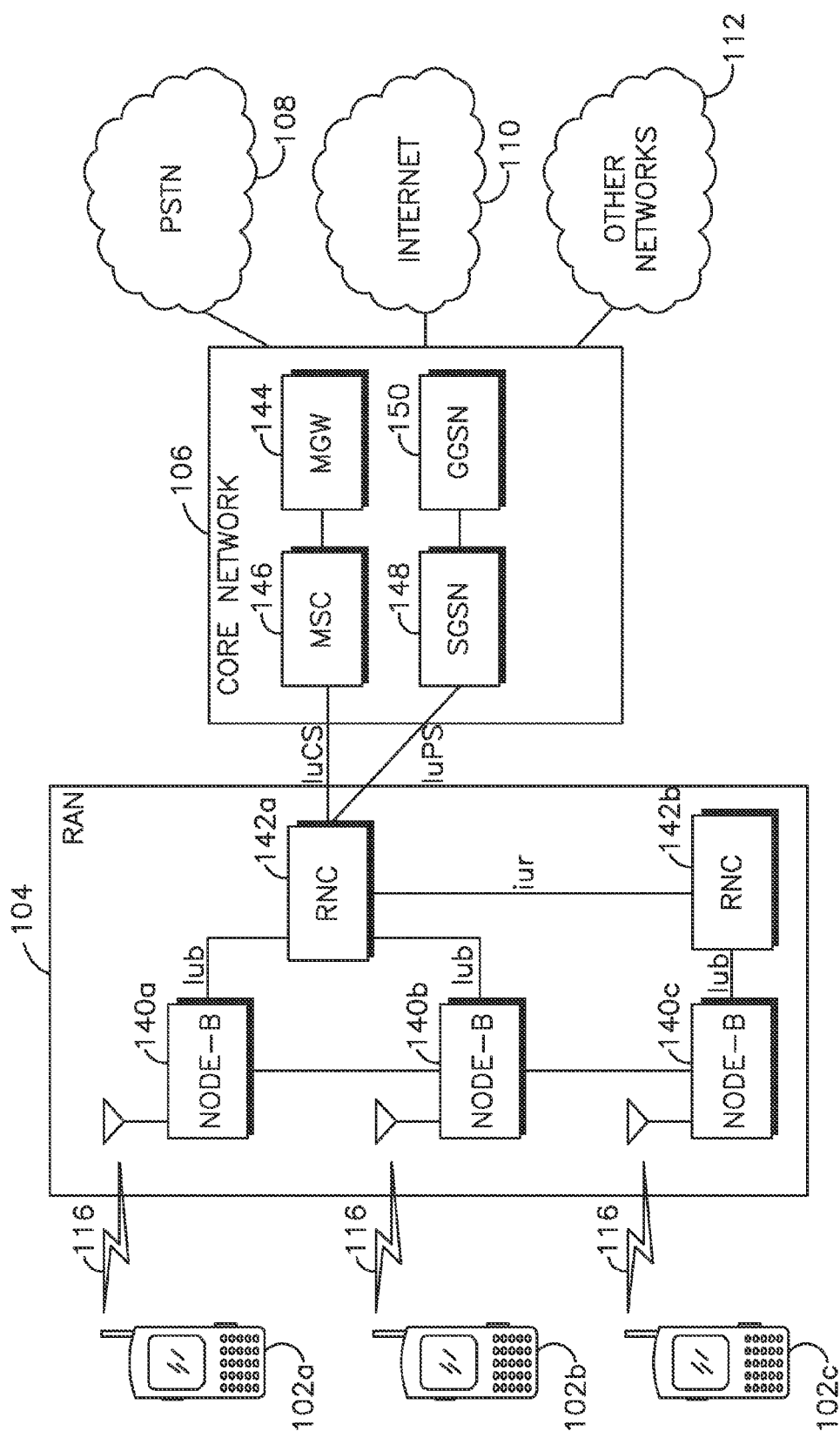
FIG. 1C is a system diagram of an example radio access network and an example core network that may be used within the communications system illustrated in FIG. 1A.

FIG. 1C is a system diagram of the RAN 104 and the core network 106 according to an embodiment. As noted above, the RAN 104 may employ a UTRA radio technology to communicate with the WTRUs 102a, 102b, 102c over the air interface 116. The RAN 104 may also be in communication with the core network 106. As shown in FIG. 1C, the RAN 104 may include Node-Bs 140a, 140b, 140c, which may each include one or more transceivers for communicating with the WTRUs 102a, 102b, 102c over the air interface 116. The Node-Bs 140a, 140b, 140c may each be associated with a particular cell (not shown) within the RAN 104. The RAN 104 may also include RNCs 142a, 142b. It will be appreciated that the RAN 104 may include any number of Node-Bs and RNCs while remaining consistent with an embodiment.

As shown in FIG. 1C, the Node-Bs 140a, 140b may be in communication with the RNC 142a. Additionally, the Node-B 140c may be in communication with the RNC 142b. The Node-Bs 140a, 140b, 140c may communicate with the respective RNCs 142a, 142b via an Iub interface. The RNCs 142a, 142b may be in communication with one another via an Iur interface. Each of the RNCs 142a, 142b may be configured to control the respective Node-Bs 140a, 140b, 140c to which it is connected. In addition, each of the RNCs 142a, 142b may be configured to carry out or support other functionality, such as outer loop power control, load control, admission control, packet scheduling, handover control, macrodiversity, security functions, data encryption, and the like.

The core network 106 shown in FIG. 1C may include a media gateway (MGW) 144, a mobile switching center (MSC) 146, a serving GPRS support node (SGSN) 148, and/or a gateway GPRS support node (GGSN) 150. While each of the foregoing elements are depicted as part of the core network 106, it will be appreciated that any one of these elements may be owned and/or operated by an entity other than the core network operator.

The RNC 142a in the RAN 104 may be connected to the MSC 146 in the core network 106 via an IuCS interface. The MSC 146 may be connected to the MGW 144. The MSC 146 and the MGW 144 may provide the WTRUs 102a, 102b, 102c with access to circuit-switched networks, such as the PSTN 108, to facilitate communications between the WTRUs 102a, 102b, 102c and traditional land-line communications devices.

The RNC 142a in the RAN 104 may also be connected to the SGSN 148 in the core network 106 via an IuPS interface. The SGSN 148 may be connected to the GGSN 150. The SGSN 148 and the GGSN 150 may provide the WTRUs 102a, 102b, 102c with access to packet-switched networks, such as the Internet 110, to facilitate communications between and the WTRUs 102a, 102b, 102c and IP-enabled devices.

As noted above, the core network 106 may also be connected to the networks 112, which may include other wired or wireless networks that are owned and/or operated by other service providers.

As described in more detail below, a communication network may include a transmitter, (e.g., source/encoder), communicating with a receiver, (e.g., destination/decoder), through a number of out-of-band relays that are connected to the decoder through capacity-constrained digital backhaul links. A transmission and relaying strategy in which multi-layer transmission is used may leverage different decoding capabilities of the relays to enable hybrid DF and CF relaying. Each relay may forward part of a decoded message and a compressed version of the received signal. Utilizing a multi-layer strategy may facilitate decoding at the destination based on the information received from the relays. In an alternate broadcast coding approach, each layer may encode an independent message. As described below, each layer may encode a selected set of independent messages.

Figure 2:
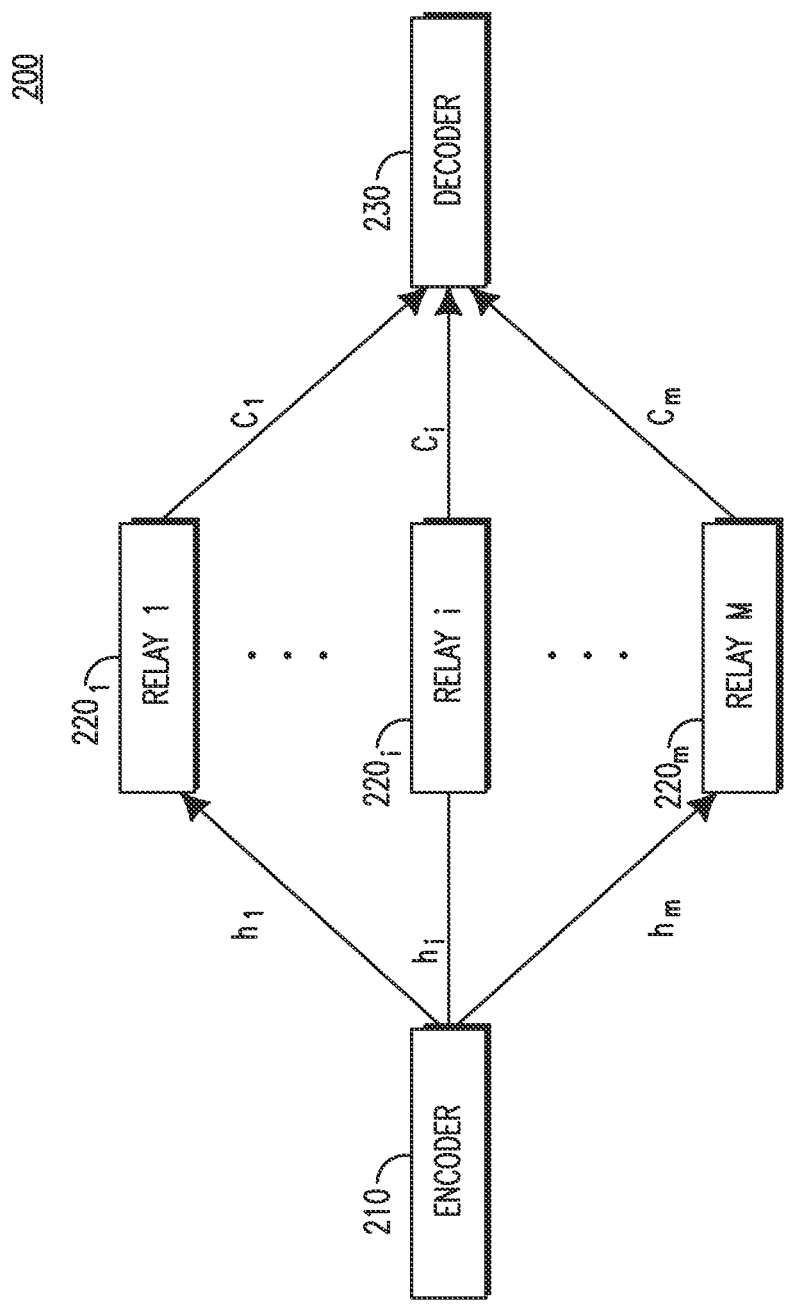
FIG. 2 is an example system diagram of a network including multiple relays in communication with and encoder and a decoder via out-of-band digital backhaul links within given capacities.

FIG. 2 is an example system diagram of a network 200 including multiple relays in communication with an encoder and a decoder via out-of-band digital backhaul links within given capacities. As shown in the system 200 of FIG. 2, an encoder 210 communicates transmissions h (designated $h_1$, $h_i$, and $h_M$) to respective relays 220 (designated $220_1$, $220_i$, and $220_M$), which transmit a respective communication along backhaul links having capacity C (designated $C_1$, $C_i$, and $C_M$) to a decoder 230. FIG. 2 shows an example communication with the multiple relays 220 connected to the decoder 230 via out-of-band digital backhaul links within given capacities. In the example network 200, $h_1 = \sqrt{g_1}e^{j\theta_1}$, $h_i = \sqrt{g_i}e^{j\theta_i}$, and $h_M = \sqrt{g_M}e^{j\theta_M}$. For purposes of example, either the encoder 210, the decoder 230, or both, may be included in a base station.

Accordingly, the network 200 depicts a variation of a multi-relay channel discussed, in which the relays 220 are connected to the destination, (i.e., decoder 230), through digital backhaul links of finite-capacity. One motivation for this model may come in the form of cloud radio cellular networks, in which the base stations may act as relays connected to a central decoder via the finite-capacity backhaul links.

A transmission strategy that is based on multi-layer transmission and hybrid relaying may be utilized as described below. Hybrid relaying may be performed by having each relay 220 forward part of the decoded messages, which may amount to partial decode-and-forward (DF), along with a compressed version of the received signal, thus adhering also to the compress-and-forward (CF) paradigm. The multi-layer strategy used at the source may be designed so as to facilitate decoding at the destination based on the information received from the relays.

The amount of information decodable at the relays 220 may depend on the generally different fading powers, (e.g., $g_1 \ldots, g_M$). To leverage the different channel qualities, flexible decoding at the relays 220 may be enabled by adopting a multi-layer transmission strategy at the encoder 210. For example, the transmitter, (i.e., encoder 210), splits its message into independent submessages or sublayers, (e.g., $W_1, \ldots, W_{M+1}$), with corresponding rates $R_1, \ldots, R_{M+1}$ in bit(s) per channel use (bit/c.u.), respectively. The idea is that message $W_1$ may be decoded by all relays 220, message $W_2$ only by relays $2, \ldots, M$, (i.e., $220_2 \ldots 220_M$), and so on. This way, relays 220 having better channel conditions may decode more information. Additionally, message $W_{M+1}$ may be instead decoded only at the destination, (i.e., decoder 230).

To encode these messages, the encoded signal may be given by $$X = \sum_{k=1}^{M+1} \sqrt{P_k}\, X_k, \qquad \text{Equation 1}$$

where the signals $X_1, \ldots, X_{M+1}$ are independent and distributed as $XN(0,1)$, and the power coefficients $P_1, \ldots, P_{M+1}$ are subject to the power constraint $\Sigma_{k=1}^{M+1} P_k \leq P$. The signal $X_1$ may encode message $W_1$, signal $X_2$ may encode both messages $W_1$ and $W_2$, and so on. Accordingly, signal $X_k$ may encode messages $W_1, \ldots, W_k$ for $k=1, \ldots, M$. Signal $X_k$ may not only encode message $W_k$, and signal $X_{M+1}$ may encode message $W_{M+1}$.

Therefore, Relay 1, (i.e., $220_1$), may decode message $W_1$ from $X_1$, while relay 2, (i.e., $220_2$), may first decode message $W_1$ from $X_1$, and then message $W_2$ from $X_2$ using its knowledge of $W_1$ and so on. Accordingly, relay k may decode messages $W_1, \ldots, W_k$ for $k=1, \ldots, M$. From standard information-theoretic considerations, the following conditions may be sufficient to guarantee that rates $R_k$ are decodable by the relays $$R_k \leq I(X_k; Y_k | X_1, \ldots, X_{k-1}), \qquad \text{Equation 2}$$

for $k=1, \ldots, M$. This may be because, in accordance with Equations 1 and 2, with $k=1$, namely $R_1 \leq I(X_1; Y_1)$, may ensure that not only relay 1, but all relays may decode message $W_1$. Generalizing, the inequality for a given k may guarantee that not only relay k may decode message $W_k$ after having decoded $W_1, \ldots, W_{k-1}$, but also all relays $k+1, \ldots, M$ may decode message $W_k$. The signal $X_{M+1}$, and thus message $W_{M+1}$ may be decoded by the destination, (i.e., decoder 230), only.

As discussed above, relay i, (i.e., $220_i$), may decode messages $W_1, \ldots, W_i$. Accordingly, each ith relay 220 may transmit partial information about the decoded messages to the destination decoder 230 via the backhaul links. In other words, each relay 220 may transmit specific subsets of the bits that make up the decoded messages. The rate at which this partial information may be transmitted to the destination decoder 230 may be selected so as to enable the decoder 230 to decode messages $W_1, \ldots, W_M$ jointly based on all the signals received from the relays 220. $C_i^{DF} \leq C_i$ may be denoted as the portion of the backhaul capacity devoted to the transmission of the messages decoded by relay i.

Beside the rate allocated to the transmission of each part of the decoded messages, relay i may utilize the residual backhaul link to transmit a compressed version $\hat{Y}_i$ of the received signal $Y_i$. The compression strategy at relay i may be characterized by the test channel $p(\hat{y}_i|y_i)$ according to conventional rate-distortion theory. Moreover, since the received signals at different relays 220 may be correlated with each other, a distributed source coding strategy may be utilized. Successive decoding may be used via, for example, Wyner-Ziv compression, with a given order $\hat{Y}_{\pi(1)} \to \ldots \to \hat{Y}_{\pi(M)}$, where $\pi(i)$ may be a given permutation of the relays 220 indices M. Thus, the decoder 230 may successfully retrieve the descriptions) $\hat{Y}_1, \ldots, \hat{Y}_M$ if the conditions $$I(Y_{\pi(i)}; \hat{Y}_{\pi(i)} | \hat{Y}_{\{\pi(1), \ldots, \pi(i-1)\}}) \leq C_{\pi(i)}^{CF} \qquad \text{Equation 3}$$

are satisfied for all i=1, . . . , M, where $C_i^{CF} \leq C_i$ may be defined as the capacity allocated by relay i to communicate the compressed received signal $\hat{Y}_i$ to the decoder 230. It may be recalled that Equation 3 is the rate needed to compress $Y_{\pi(i)}$ as $\hat{Y}_{\pi(i)}$ given that the destination has side information given by the previously decompressed signals $\hat{Y}_{\pi(1)}, \ldots, \hat{Y}_{\pi(i-1)}$.

A Gaussian test channel $p(\hat{y}_i|y_i)$, may be utilized so that the compressed signal $\hat{Y}_i$ may be expressed as:

$$\hat{Y}_i = Y_i + Q_i, \qquad \text{Equation 4}$$

where the compression noise $Q_i$: $XN(0, \sigma_i^2)$) may be independent of the received signal $Y_i$ to be compressed.

The destination decoder 230 may first recover the descriptions $\hat{Y}_i, \ldots, \hat{Y}_M$ from the signals received by the relays 220. This step may be dependent that the conditions in Equation 3 are satisfied. Having obtained $\hat{Y}_M = \{\hat{Y}_1, \ldots, \hat{Y}_M\}$, the destination, (i.e., decoder 230), may jointly decode the messages $W_1, \ldots, W_M$ based on the partial information about these messages received from the relays 220 and on the compressed received signals $\hat{Y}_M$. Finally, message $W_{M+1}$ may be decoded.

Figure 3:
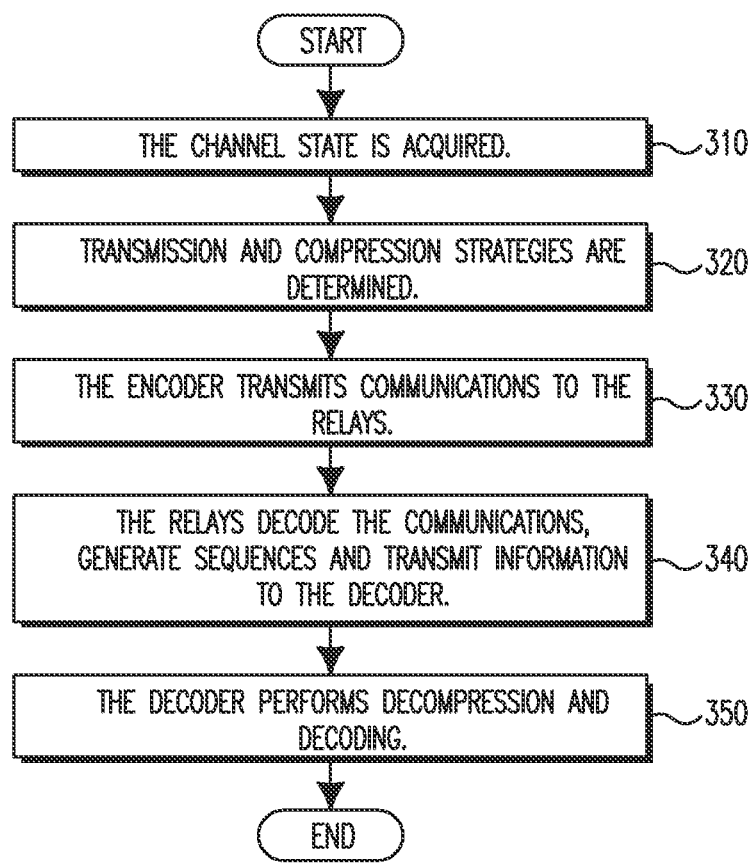
FIG. 3 is a flow diagram of an example method of multilayer transmission with hybrid relaying.

FIG. 3 is a flow diagram of an example method 300 of multilayer transmission with hybrid relaying. FIG. 3 is an example of a hybrid DF-CF relaying.

In step 310, the channel state is acquired. For example, relay $220_i$, (relay i), may estimate channel $h_i$ for i=1, . . . , M. The relay i may report its channel $h_i$ to the decoder 230 for i=1, . . . , M.

Transmission and compression strategies may be determined in step 320. For example, the decoder 230 may compute power allocations $P_1, \ldots, P_{M+1}$, compression strategies $\beta_1, \ldots, \beta_M$, and the ordering $\pi$ for decompression as described above. The decoder 230 may inform the encoder 210 about the obtained power allocations $P_1, \ldots, P_{M+1}$. Additionally, the decoder 230 may inform relay $220_i$ (relay i), about the obtained compression strategy $\beta_i$ for i=1, . . . , M. The rate $R_k$ and corresponding modulation and coding strategy $ENC_k$ to be used for layer k for k=1, . . . , M+1 may be computed by the decoder 230 and it may inform the encoder 210 and relay $220_i$, (relay i) about the rate $R_i$ and coding strategy $ENC_i$ for i=1, . . . , M, as well as informing the encoder 210 about the rate $R_{M+1}$ and coding strategy $ENC_{M+1}$.

In step 330, the encoder 210 transmits communications to the relays 220. For example, the encoder 210, for a message $W_k 1 \in \{1, \ldots, 2^{nR_k}\}$ for k=1, . . . , M+1, may build codewords $\{X_{k,t}\}_{t=1}^n = ENC_k(W_1, \ldots, W_k)$ for k=1, . . . , M and $\{X_{M+1,t}\}_{t=1}^n = ENC_{M+1}(W_{M+1})$. The encoder 210 may transmit the signal $$X_t = \sum_{k=1}^{M+1} \sqrt{\frac{P X_{k,t}}{\cdot k}}$$

in channel use for t=1, . . . , n. Relay $220_i$, (relay i) may receive signal $Y_{i,t} = h_i X_t + Z_t$ for t=1, . . . , n.

In step 340, the relays 220 decode the communications, generate sequences and transmit information to the decoder 230. For example, Relay $220_i$, (relay i) may decode messages $W_1, \ldots, W_i$ based on the sequence $\{Y_{i,t}\}_{t=1}^n$ for i=1, . . . , M, and may generate the sequence $\{\hat{Y}_{i,t}\}_{t=1}^n$ with each signal $\hat{Y}_{i,t}$ obtained by quantizing $Y_{i,t}$ with noise $Q_{i,t} \sim CN(0, \beta_i^{-1}-1)$, for example, $\hat{Y}_{i,t} = Y_{i,t} + Q_{i,t}$ for i=1, . . . , M. Relay $220_i$, (relay i) may also transmit partial information about the decoded messages $W_1, \ldots, W_i$ and the index associated with the sequence $\{\hat{Y}_{i,t}\}_{t=1}^n$ to the decoder 230 via backhaul link of capacity $C_i$ for i=1, . . . , M.

In step 350, the decoder 230 performs decompression and decoding, the decoder 230 may first recover the signals for $\{\hat{Y}_{i,t}\}_{t=1}^n$ for i=1, . . . , M with the ordering $\{\hat{Y}_{i,t}\}_{t=1}^n \to \ldots \to \{\hat{Y}_{\pi(M),t}\}_{t=1}^n$ based on the indices collected from the relays 220. The decoder 230 may decode jointly the message $W_1, \ldots, W_M$ based on the partial information received from the relays 220 and on the compressed signals $\{\hat{Y}_{i,t}\}_{t=1}^n$ for i=1, . . . , M. Finally, the decoder 230 may decode the message $W_{M+1}$ based on the signals $\{\hat{Y}_{i,t}\}_{t=1}^n$ for i=1, . . . , M and the decoded messages $W_1, \ldots, W_M$.

Below are examples of numerical results of a multi-layer transmission scheme with hybrid relaying described above as compared to conventional schemes. For reference, achievable rates may also be compared with the cutset upper bound $$R_{cutset} = \min_{\Sigma \subseteq \{1,\ldots,M\}} \left\{ \sum_{j \in \Sigma} C_j + \log\left(1 + P \sum_{j \in \Sigma^c} g_j\right) \right\}. \qquad \text{Equation 5}$$

For purposes of example, the case with two relays may be focused on, for example, M=2. Single-layer schemes may be marked with the label 'SL' and multi-layer schemes with 'ML'. For CF related schemes, the optimal ordering $\pi^{opt}$ may be found via exhaustive search and may be observed to be $\pi=(1,2)$ for all the simulated cases.

Figure 4:
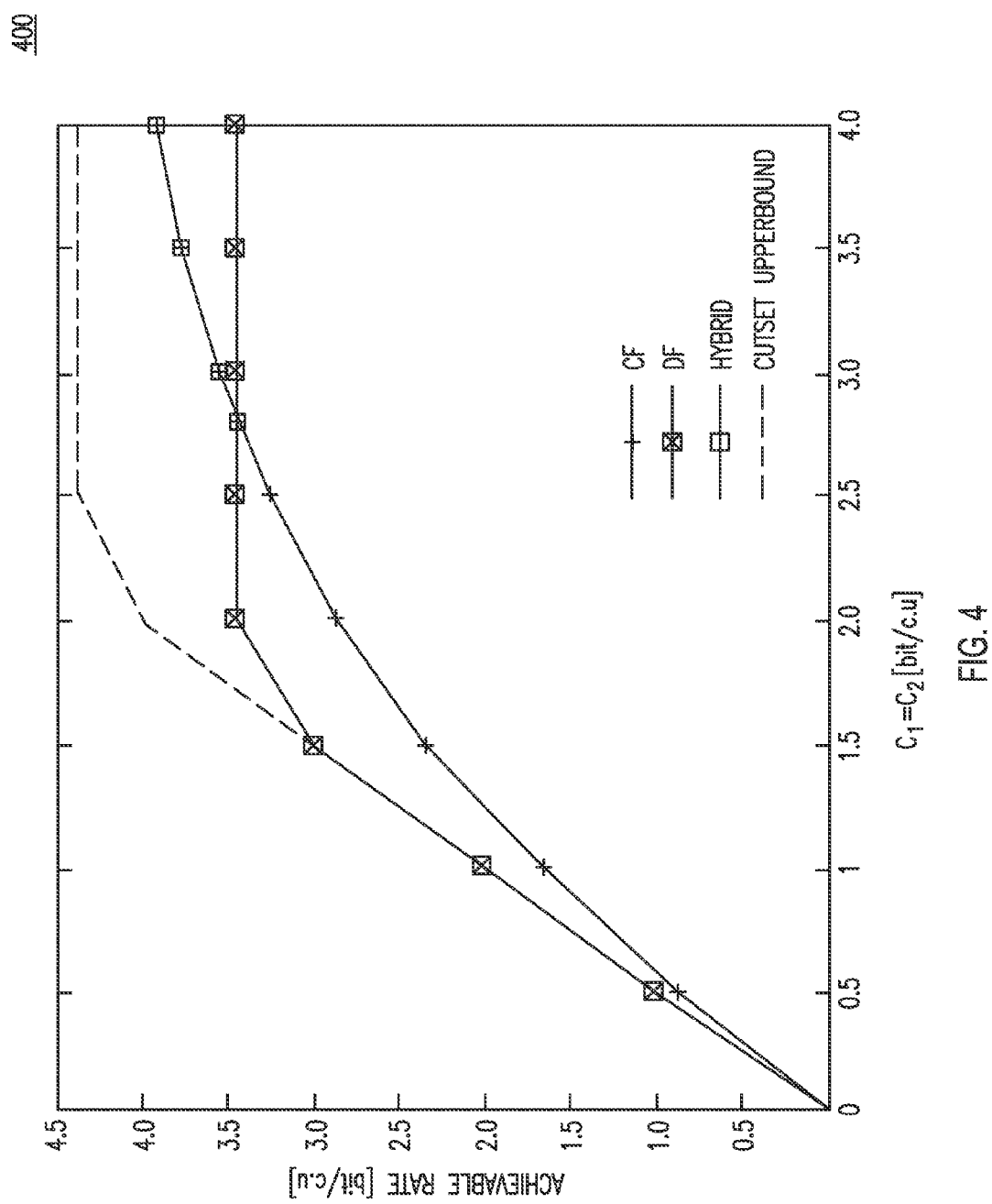
FIG. 4 is an example diagram depicting achievable rates versus the backhaul capacity $C_1=C_2$ in a symmetric network with M=2, P=0 dB, and $g_1=g_2=10$ dB.

FIG. 4 is an example diagram 400 depicting achievable rates versus the backhaul capacity $C_1 = C_2$ in a symmetric network with M=2, P=0 dB, and $g_1 = g_2 = 10$ dB. As shown in FIG. 4, the performance in a symmetric setting may be examined by plotting the rate versus the backhaul capacities $C_1 = C_2$ when P=0 dB and $g_1 = g_2 = 10$ dB. In this symmetric set-up, the optimized hybrid scheme may end up reducing to either the DF or the CF strategy at small and large backhaul capacity, respectively. The single-layer and multi-layer strategies may not be distinguishable since they show the same performance when the relays experience the same fading power, for example, $g_1 = g_2$. This may be a result of multi-layer strategies being relevant only when two relays have different decoding capabilities.

Figure 5:
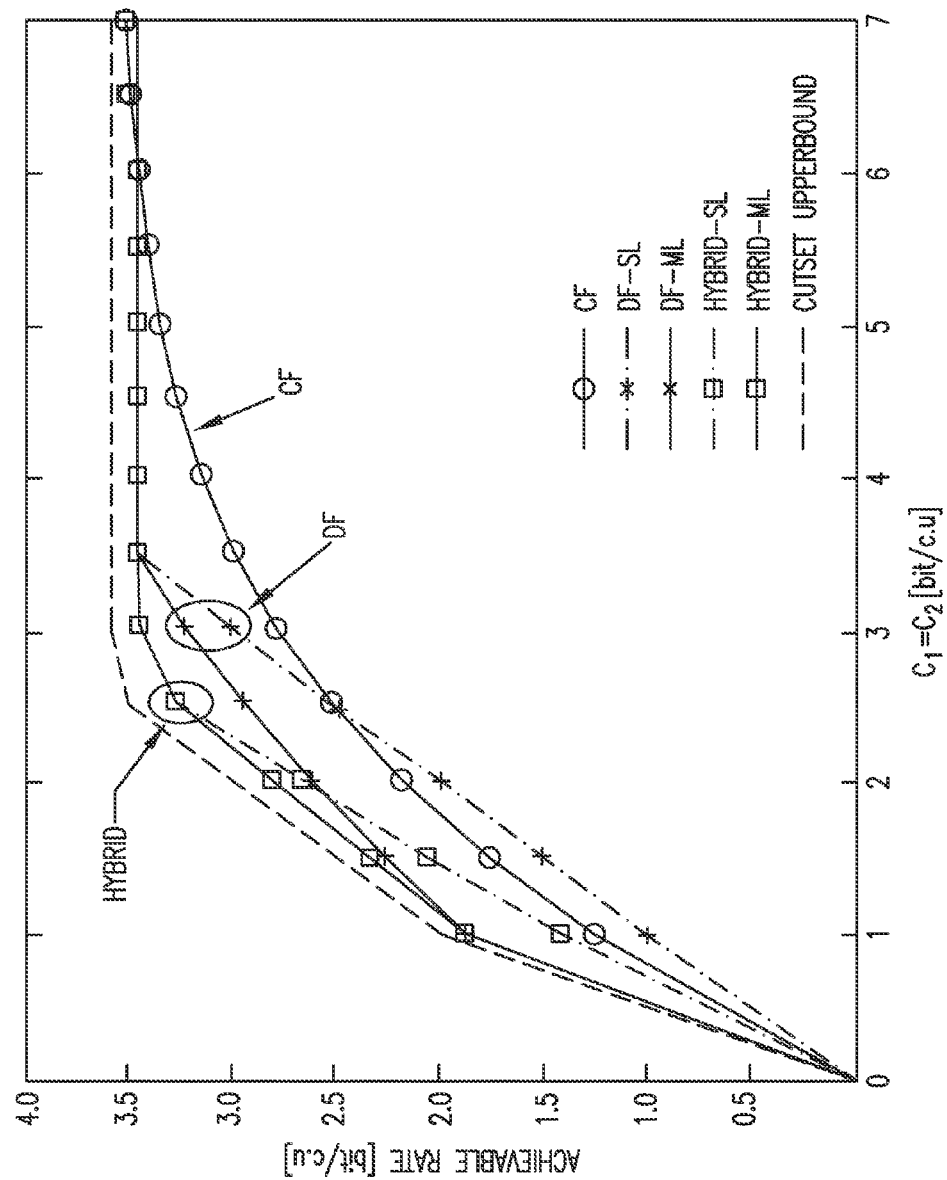
FIG. 5 is an example diagram depicting achievable rates versus the back haul capacity $C_1=C_2$ per relay with M=2, P=0 dB, and $[g_1, g_2]=[0.10]$dB.

FIG. 5 is an example diagram 500 depicting achievable rates versus the back haul capacity $C_1 = C_2$ per relay with M=2, P=0 dB, and $[g_1, g_2] = [0.10]$ dB. As shown in FIG. 5, the performance may be observed versus the backhaul $C_1 = C_2$ with P=0 dB and asymmetric channel powers $[g_1, g_2] = [0.10]$ dB. Unlike the symmetric setting in FIG. 4, the multi-layer strategy may be beneficial compared to the single-layer (SL) transmission for both DF and Hybrid schemes. Moreover, unlike the setting of FIG. 4, the hybrid relaying strategy may show a performance advantage with respect to all other schemes. This may be the case for intermediate values of the backhaul capacities $C_1 = C_2$. It may also be mentioned that, as $C_1 = C_2$ increases, the performance of DF schemes may be limited by the capacity of the better decoder, namely $\log_2(1+10) = 3.46$ bit/c.u., while CF, and thus also the hybrid strategy, are able, for $C_1 = C_2$ large enough, to achieve the cutset bound.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. Examples of computer-readable media include electronic signals (transmitted over wired or wireless connections) and computer-readable storage media. Examples of computer-readable storage media include, but are not limited to, a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs). A processor in association with software may be used to implement a radio frequency transceiver for use in a WTRU, UE, terminal, base station, RNC, or any host computer.

What is claimed:

1. A method for use in a relay performing hybrid multi-layer transmission, comprising:
   receiving a multi-layer signal from a source device, wherein the multi-layer signal includes a plurality of sublayers, wherein each sublayer of the multi-layer signal is subject to a power constraint;
   decoding a quantity of the plurality of sublayers based at least upon a channel quality between the relay and the source device;
   generating a quantization sequence associated with the received multi-layer signal;
   compressing the received multi-layer signal, wherein the compression includes a compression index associated with the quantization sequence; and
   transmitting information relating to the decoded sublayers, the compressed multi-layer signal, and the compression index associated with the quantization sequence to a destination device.

2. The method of claim 1 wherein the information includes a subset of bits that comprise the decoded sublayers.

3. The method of claim 1 wherein the source device is an encoder.

4. The method of claim 1 wherein the destination device is a decoder.

5. A relay, comprising:
   at least one circuit configured to receive a multi-layer signal from a source device, wherein the multi-layer signal includes a plurality of sublayers, wherein each sublayer of the multi-layer signal is subject to a power constraint;
   the at least one circuit configured to decode a quantity of the plurality of sublayers based at least upon a channel quality between the relay and the source device;
   the at least one circuit configured to generate a quantization sequence associated with the received multi-layer signal;
   the at least one circuit configured to compress the received multi-layer signal, wherein the compression includes a compression index associated with the quantization sequence; and
   the at least one circuit configured to transmit information relating to the decoded sublayers, the compressed multi-layer signal, and the compression index associated with the quantization sequence to a destination device.

6. The relay of claim 5 wherein the information includes a subset of bits that comprise the decoded sublayers.

7. The relay of claim 5 wherein the source device is an encoder.

8. The relay of claim 5 wherein the destination device is a decoder.

* * * * *